United States Patent [19]

Kanshin et al.

[11] Patent Number: 4,567,891

[45] Date of Patent: Feb. 4, 1986

[54] DEVICE FOR ESTABLISHING COMPRESSION ANASTOMOSES

[76] Inventors: Nikolai N. Kanshin, ulitsa Malaya Filevskaya, 68, kv. 10; Vladimir M. Fedotov, ulitsa Startovaya, 21, kv. 42; Boris A. Smirnov, ulitsa Borisa Galushkina, 17, kv. 26, all of Moscow, U.S.S.R.

[21] Appl. No.: 635,467

[22] Filed: Jul. 27, 1984

Related U.S. Application Data

[63] Continuation of Ser. No. 336,176, Dec. 31, 1981, abandoned.

[51] Int. Cl.[4] ............................................. A61B 17/04
[52] U.S. Cl. .............................. 128/334 C; 128/334 R
[58] Field of Search ............... 128/334 R, 334 C, 305, 128/328, 356

[56] References Cited

U.S. PATENT DOCUMENTS 4,055,186 10/1977 Leveen .................... 128/334 C

FOREIGN PATENT DOCUMENTS 357306 8/1922 Fed. Rep. of Germany ... 128/334 C
1057729 5/1959 Fed. Rep. of Germany ... 128/334 C Primary Examiner—Stephen C. Pellegrino
Assistant Examiner—Gene B. Kartchner
Attorney, Agent, or Firm—Burgess, Ryan & Wayne

[57] ABSTRACT

A compression anastomoses device has a first bush coaxially arranged with a second bush. The first bush has a flange at one end and a collet at the other end. The second bush is adapted to slide over the surface of the first bush and provided with a movable spring-actuated ring. The second bush is covered from outside by an elastic sheathing that passes into a two-lumen tube, one of the tube lumens communicating with the interior of the elastic sheathing, while the other lumen opens outwards immediately above the sheathing.

6 Claims, 4 Drawing Figures

U.S. Patent  Feb. 4, 1986  4,567,891
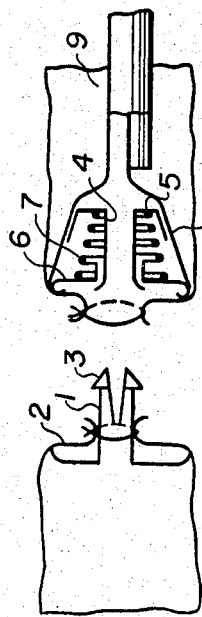
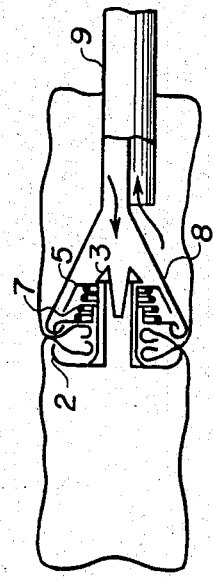
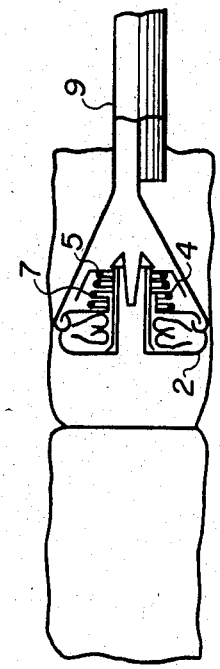
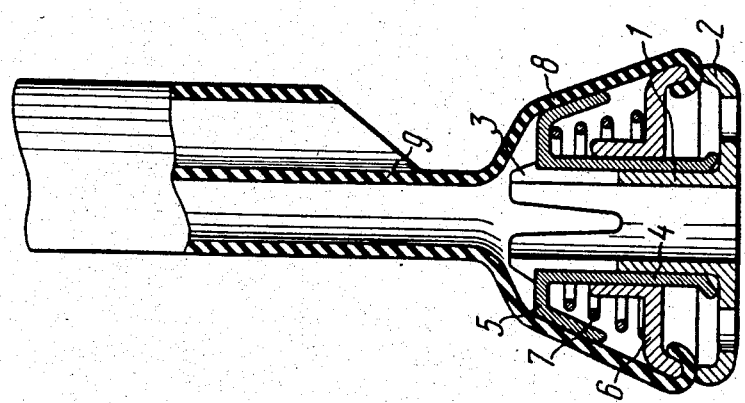

DEVICE FOR ESTABLISHING COMPRESSION ANASTOMOSES

This is a continuation of U.S. Ser. No. 336,176 filed Dec. 31, 1981, now abandoned.

FIELD OF THE INVENTION

The present invention relates generally to medical engineering, and more specifically to devices for uniting hollow organs and particularly to devices for establishing compression anastomoses in the alimentary tract.

BACKGROUND OF THE INVENTION

Prior-art devices for establishing compression anastomoses (cf. e.g., "Sutureless Anastomoses in Surgery of the Gastrointestinal Tract with and without Static Magnetic Field" by N. N. Kanshim et al., Archive of pathology, 1978, v. XL, issue 8, pp. 56–61) are known to be shaped as rings of a magnetic material. However, such devices feature a considerable weight, are rigid and poorly migrate along the intestine after having been cast off, thus causing serious complications rather frequently.

One prior-art suturing instrument for establishing compression anastomoses in the gastrointestinal tract (cf. Certificate of Instrument AKA-2 manufactured by the Moscow electromedical equipment plant, Int. cl. A61b 17/11) is known to comprise a tubular body carrying a ring with needles, a supporting head carrying a connecting ring, a mechanical actuator for the supporting head to travel relatively to the body, and a circular knife. The instrument is suitable for connecting the interior spaces of the organs being sutured by means of rings providing for compression along the line of suture, followed by removal of the rings by natural function.

The aforesaid instrument, however, fails to establish anastomoses in the upper alimentary tract on account of more traumatic insertion of its components into the cavity of the organs operated upon, and the rings might become stuck when migrating along the gastrointestinal tract. Moreover, oral extraction of the rings is impossible.

One more device for establishing compression anastomoses, the so-called Murphy's button, is known to comprise coaxially arranged a flanged bush fittable into second flanged bush provided with a ring slidable over the surface thereof and with a spring interposed between the ring and flange. The second of said bushes has an inside diameter allowing it to slide over the external surface of the first bush. The device has a retainer to fix the both bushes with respect to each other when joined together (cf. "Murphy's Button and Its Modifications", a thesis by L. G. Stuckey, 1903, St. Petersburg).

The aforesaid device is a small-size one enabling compression anastomoses to be established in the lower alimentary tract. It becomes more and more urgent and promiseful as a medical tool due to the use of up-to-date light and stainless metals and materials as well as due to high-quality compression anastomoses and good postoperative healing of the united intestine walls with its use.

However, the Murphy's button suffers from a number of substantial disadvantages.

When establishing gastroesophagostomy and especially gastroenterostomy, the button cannot be removed by the oral route after firm union has occurred between the tissues operated upon and the button has slough away. However, when freely migrating along the intestine the button might get stuck therein, thus causing an occlusion ileus or necrotic ulceration of the intestinal wall within the area of the stuck button. Moreover, the Murphy's button fails to provide simultaneous decompression of the anastomotic zone and early enteral feeding through a feeding tube within the postoperative period.

SUMMARY OF THE INVENTION

It is an object of the present invention to provide an improved device of the type described wherein early tube feeding within the postoperative period following the establishing of a compression anastomosis.

It is another object of the present invention to provide an improved device of the type described wherein decompression within the anastomotic zone simultaneously with early tube feeding of the patient can be carried out.

It is one more object of the present invention to provide a device of the type described wherein extraction of a possibility of freely extracting the device by the oral route (after its having been cast off) can be freely made.

The aforesaid objects are accomplished due to the fact that in a device for establishing compression anastomoses having coaxially arranged a first flanged bush, and a second flanged bush having an inside diameter allowing it to slide over the external surface of said first bush, and including a ring mounted slidably over the external surface of said second bush, and a spring interposed between the ring and flange of the second bush, as well as a retainer for fixing the mutual position of the bushes, the second bush is according to the present invention, covered by an elastic sheathing that passes into a tube.

In order to effect decompression within the anastomotic zone simultaneously with early tube feeding, it is expedient that the aforesaid tube of elastic sheathing be made double-lumen so that one of the lumens thereof be communication with the interior of the elastic sheathing, while the other lumen opens outwards immediately above the sheathing.

The device for establishing compression anastomoses according to the present invention is simple in construction and application technique, inexpensive, is capable of establishing good anastomoses involving minimized traumatic lesion to the organs operated upon, is easy to extract from the alimentary tract, enables early tube feeding of the patient simultaneously with decompression within the anastomotic zone, and provides for favourable conditions within the anastomotic zone for the healing process.

BRIEF DESCRIPTION OF THE DRAWINGS

In what follows the present invention is illustrated by a detailed description of a specific embodiment thereof with reference to the accompanying drawings, wherein:

FIG. 1 is a partially sectioned view of the device for establishing compression anastomoses, generally showing its bushes joined together;

FIG. 2 is a schematic view of the intestine ends with the bushes inserted into them before joining said bushes together;

FIG. 3 is a schematic view of the united intestine ends; and

FIG. 4 is a schematic view of removing the device from the alimentary tract after its having been cast off

DETAILED DESCRIPTION OF THE INVENTION

The device for establishing compression anastomoses comprises a bush 1 (FIG. 1) with a flange 2 at one end and a collet 3 at the other. Fitted over the bush 1 coaxially therewith is a bush 4 with a flange 5, said bush having an inside diameter enabling it to slide over the external surface of the bush 1. The bush 4 has a coaxial ring 6 slidably mounted over the external surface of the bush 4, and a spring 7 thrusting with its one end against the flange 5 and with the other, against the ring 6.

On the outside the bush 4 is covered with an elastic sheathing 8 that passes into a tube 9. The tube 9 may be either a single- or double-lumen one, which is the case with FIG. 1. In the second case one of the lumens of the tube 9 communicates with the interior of the sheathing 8, while the other lumen opens outwards immediately above the sheathing 8.

The collet 3 serves as a retainer of the mutual position of the bushes 1 and 4 when joined together as seen in FIG. 1.

The device for establishing compression anastomoses according to the present invention operates as follows.

Originally the bushes 1 (FIG. 2) and 4 are disjoined. Then the bush 4 is introduced into the cavity of the proximal portion of the organ operated upon, e.g., an intestine, after having preliminarily passed the tube 9 through the alimentary tract and bringing it outwards through the mouth or nasal cavity. Next a ligature is applied to the intestine end immediately past the inserted bush 4 to form a purse-like pattern, leaving a clear opening approximately equal to the diameter of the bush 1. Then the bush 1 is inserted into the cavity of the distal portion of the intestine operated upon and the intestine end is ligated round the flange 2 to form a purse-like pattern so that the bush end with the collet 3 (FIG. 2) should project outwards. Thereupon the projecting end of the bush 1 with the collet 3 is introduced into the bush 4 through the appropriate hole all the way in. As a result the bushes 1 and 4 become joined permanently together by means of the collet 3. Thus, the intestine ends are united (FIG. 3). Next the intestinal walls start to be compressed round the anastomotic perimeter by the edges of the flange 2 and the ring 6 under the action of the spring 7 that has been compressed when the bushes 1 and 4 have been joined together. Thus, the outer layers of the intestinal walls are united, whereas the inner necrotic layers thereof slough away. It is due to the provision of the double-lumen tube 9 that early tube feeding of the patient is carried out within that period and favourable conditions for the healing process are provided within the anastomotic zone due to decompression effected through the other tube lumen. In the case of the single-lumen tube 9 a decompressing catheter is periodically introduced into the anastomotic zone for decompression purposes. After a certain period of time the process terminates in a primary union of the intestinal walls and in a complete casting off of the necrotized tissues compressed by the device.

Once the device has been cast off completely it is extracted from the intestinal cavity by pulling out the tube 9. Owing to the fact that the elastic sheathing 8 acquires a taper shape when pulling at the tube 9, the device passes freely through the cardiac sphincter and is easily extracted from the alimentary tract by the oral route (FIG. 4).

What is claimed is:

1. A device for establishing compression anastomoses comprising a first hollow tubular bush, having a flange at its distal end, a second bush slidable coaxially over said first bush and having a radially outward collar at its proximal end, means for coupling said bushes in their coaxial position, comprising a ring freely slidable coaxially over said second bush and having a circular edge at its distal end lying in opposition to said flange when said bushes are coupled, spring means arranged between said collar and said ring for normally biasing said ring distally, to cause said circular edge to press against said flange, and a conduit extending proximally from said second bush and having an elastic sheath extending distally fitting over the collar of said second bush and ring edge to be clamped between said ring edge and said flange, said conduit including a pair of tubes, the first of said tubes extending through said sheath in communication with the hollow tubular bush, the second of said tubes terminating exteriorly of said sheath, said flange of said first bush being introducable into the lumen of the distal section of the severed intestine, the second bush and ring being introducable into the lumen of the proximal section of the severed intestine with the attached conduit extending outward of said intestine through an oral opening and the bushes thereafter coupled together with the ends of the lumens compressed between the elastich sheath and said flange, to effect anastomosis, said device being removable from said intestine, after anastomosis, by withdrawal of said conduit through said oral opening.

2. The device according to claim 1, wherein said spring means comprises a helical spring surrounding said second bush.

3. The device according to claim 1, wherein said collar comprises a radially outward and conically downwardly directed flange providing a tapered surface in the proximal direction for said sheath.

4. The device according to claim 1, wherein said coupling means comprises a collet formed at the proximal end of said first bush adapted to engage over the proximal end of said second bush.

5. The device according to claim 1, wherein said ring is provided with an elongated tubular hub slidable on said second bush.

6. A device for establishing compression anastomoses comprising:
   a first hollow tubular bush having a flange at its distal end;
   a second bush slidable coaxially over said first bush and having a radially outward collar at its proximal end;
   means for coupling said bushes intheir coaxial position, including a ring freely slidable coaxially over said second bush and having a circular edge at its distal end lying in opposition to said flange when said bushes are coupled, spring means arranged between said collar and said ring for normally biasing said ring distally, to cause said circular edge to press against said flange, and a collet formed at the proximal end of said first bush adapted to engage over the proximal end of said second bush, said collet including a plurality of radial outwardly biased fingers each terminating in a flange for engaging over the proximal end of the radially outward collar to lock said first and second bushes together; and a conduit extending proximally from and in communication with said second bush;

said flange of said first bush being introducable into the lumen of the distal section of the severed intestine, the second bush and ring being introducable into the lumen of the proximal section of the severed intestine with the attached conduit extending outward to said intestine through an oral opening and the bushes thereafter coupled together with the ends of the lumens compressed between said ring and said flange, to effect anastomosis, said device being removable from said intestine, after anastomosis, by withdrawal of said conduit through said oral opening.

* * * * *